US008541738B2

(12) United States Patent
Tona et al.

(10) Patent No.: US 8,541,738 B2
(45) Date of Patent: Sep. 24, 2013

(54) SURFACE ANALYZER OF OBJECT TO BE MEASURED AND ANALYZING METHOD

(75) Inventors: Masahide Tona, Tokyo (JP); Shunsuke Ohtani, Tokyo (JP); Makoto Sakurai, Hyogo (JP)

(73) Assignees: Japan Science and Technology Agency, Saitama (JP); The University of Electro-Communications, Tokyo (JP); National University Corporation Kobe University, Hyogo (JP)

( * ) Notice: Subject to any disclaimer, the term of this patent is extended or adjusted under 35 U.S.C. 154(b) by 266 days.

(21) Appl. No.: 12/937,253

(22) PCT Filed: Apr. 7, 2009

(86) PCT No.: PCT/JP2009/057121
§ 371 (c)(1),
(2), (4) Date: Dec. 27, 2010

(87) PCT Pub. No.: WO2009/125761
PCT Pub. Date: Oct. 15, 2009

(65) Prior Publication Data
US 2012/0061564 A1    Mar. 15, 2012

(30) Foreign Application Priority Data

Apr. 9, 2008   (JP) .................................. 2008-101984

(51) Int. Cl.
*G01N 23/225*   (2006.01)
(52) U.S. Cl.
CPC .................................. *G01N 23/2258* (2013.01)
USPC .......................................... 250/307; 250/309
(58) Field of Classification Search
USPC ................................................. 250/307, 309
See application file for complete search history.

(56) References Cited

U.S. PATENT DOCUMENTS 6,288,394 B1 *  9/2001  Barnes et al. ................... 850/43
7,005,685 B2 *  2/2006  Sakai et al. ..................... 257/103
(Continued)

FOREIGN PATENT DOCUMENTS

| JP | 63-184255 A | 7/1988 |
| JP | 2004-037120 A | 2/2004 |
| JP | 2005-019537 A | 1/2005 |

OTHER PUBLICATIONS

McDonald et al., "Observation of High Electron Emission Yields following Highly Charged Ion Impact (up to Th75+) on Surfaces", Phys. Rev. Lett., Apr. 13, 1992, vol. 68, No. 15, p. 2297-2300 Mentioned on pp. 1 and 3 of the as-filed specification.

(Continued)

*Primary Examiner* — Jack Berman
*Assistant Examiner* — Eliza Osenbauch-Stewart
(74) *Attorney, Agent, or Firm* — Chen Yoshimura LLP

(57) ABSTRACT

A surface analyzer 1 includes: a sample stage 6 for placing a sample 5; a source for generating multicharged ions 3 for irradiating a beam 4 of multicharged ions having a valence of 15 or higher to the sample 5 placed on the sample stage 6; a mass analyzer 8 for detecting secondary ions 7 generated as a result of irradiating the beam of multicharged ions 4 to the sample 5; a secondary electron detector 10 for detecting secondary electrons 9 generated as a result of irradiating the beam of multicharged ions 4 to the sample 5; and a controller of mass analyzer 12 for generating analysis start signals in response to the secondary electron signals received, and transmitting the start signals to the mass analyzer. The surface analyzer 1 enables high-quality analysis of the surface of the sample in short time by using the multicharged ions.

4 Claims, 16 Drawing Sheets

(56) References Cited

U.S. PATENT DOCUMENTS 7,193,206 B2 * 3/2007 Bai et al. ................. 250/288
2007/0267565 A1 11/2007 Nishizawa et al.

OTHER PUBLICATIONS

Meguro et al., "Creation of nanodiamonds by single impacts of highly charged ions upon graphite", Appl. Phys. Lett., Dec. 3, 2001, vol. 79, No. 23, p. 3866-3868 Mentioned on pp. 1 and 3 of the as-filed specification.

Schenkel et al., "Solid state quantum computer development in silicon with single ion implantation", Journal of Applied Physics, Dec. 1, 2003, vol. 94, No. 11, p. 7017-7024 Mentioned on pp. 1 and 3 of the as-filed specification.

Kobayashi et al., "Design and Construction of a Horizontally Placed Superconducting Magnet and its Cryostat for an Electron Beam Ion Source", Institute of Plasma Laboratory at Nagoya University, Data and Technical Report IPPJ-DT-84, 1981 Mentioned on pp. 2 and 3 of the as-filed specification.

Levine et al., "The Electron Beam Ion Trap: A New Instrument for Atomic Physics Measurements", Physica Scr., 1988, vol. T22, p. 157-163 Mentioned on pp. 2 and 3 of the as-filed specification.

Ohtani et al., "Researches on Highly Charged Ions Using Electron Beam Ion Traps", The Journal of the Japan Society of Plasma Science and Nuclear Fusion Research, Oct. 1997, vol. 73, No. 10, p. 1063-1079 Mentioned on pp. 2 and 3 of the as-filed specification.

Yamazaki, "High sensitive detection of surface-adsorbed hydrogen atoms with slow highly charged ions", The 52nd Spring Meeting, The Japan Society of Applied Physics and Related Societies, 2005, No. 0, 29p-C-3 Mentioned on p. 3 of the as-filed specification as a concise explanation of relevance.

Tona et al., "Some characteristics in the interaction of slow highly charged Iq+ ions with a Si(111) 1x1-H surface", Surface Science, Nov. 21, 2005, vol. 600, pp. 124-132.

Takahashi et al., "Toward over unity proton sputtering yields from a hydrogen-terminated Si(111) 1X1 surface irradiated by slow highly charged Xe ions", Apllied Physics Letters, Aug. 3, 2005, vol. 87, No. 6, Doc. ID063111-1-ID063111-3, downloaded on May 7, 2009.

International Search Report (ISR) issued in PCT/JP2009/057121 mailed in May 2009 for Examiner consideration, citing U.S. Patent Application Publication No. 1, Foreign Patent document Nos. 1-3 and Non-Patent literature Nos. 8-9 listed above.

Written Opinion (PCT/ISA/237) issued in PCT/JP2009/057121 mailed in May 2009. Concise Explanation of Relevance: This Written Opinion considers the claims are not described by or obvious over the Foreign Patent document Nos. 1-3 and Non-patent literature Nos. 8-9 cited in ISR above.

\* cited by examiner (A)

(B)

| AND INPUT | | AND OUTPUT |
|---|---|---|
| 24A | 24B | 24C |
| 1 | 1 | 1 |
| 1 | 0 | 0 |
| 0 | 1 | 0 |
| 0 | 0 | 0 |

F I G . 8
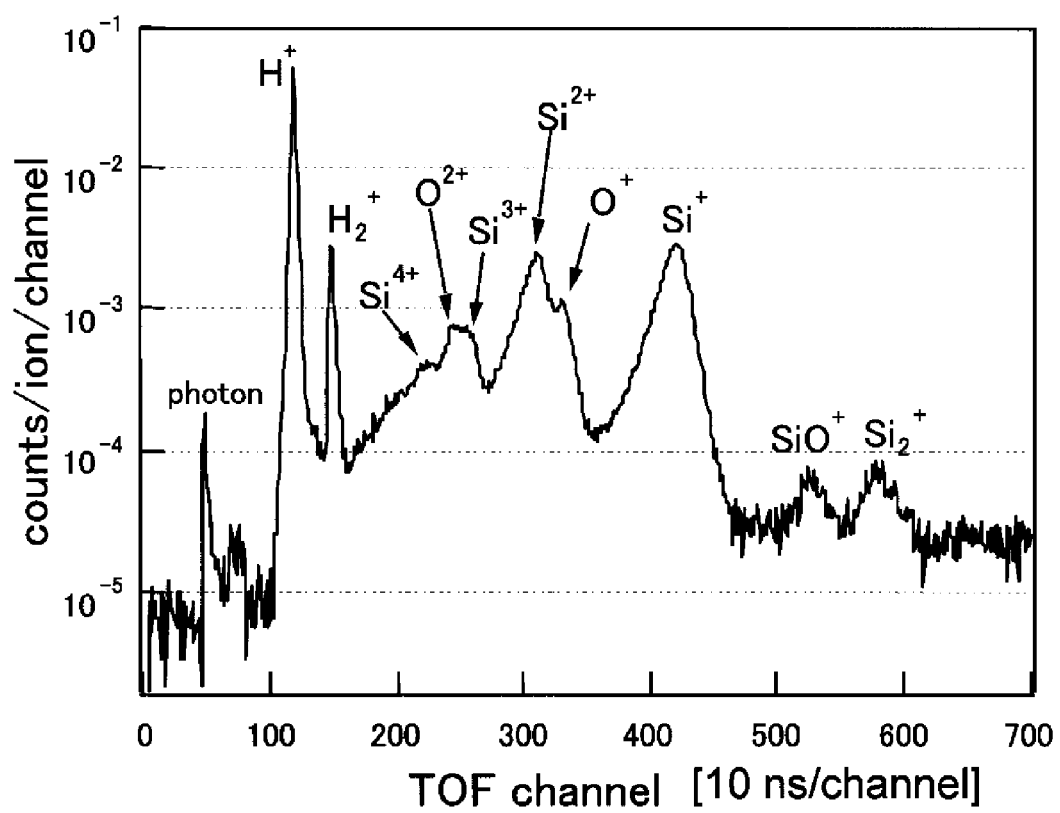

F I G. 1 0
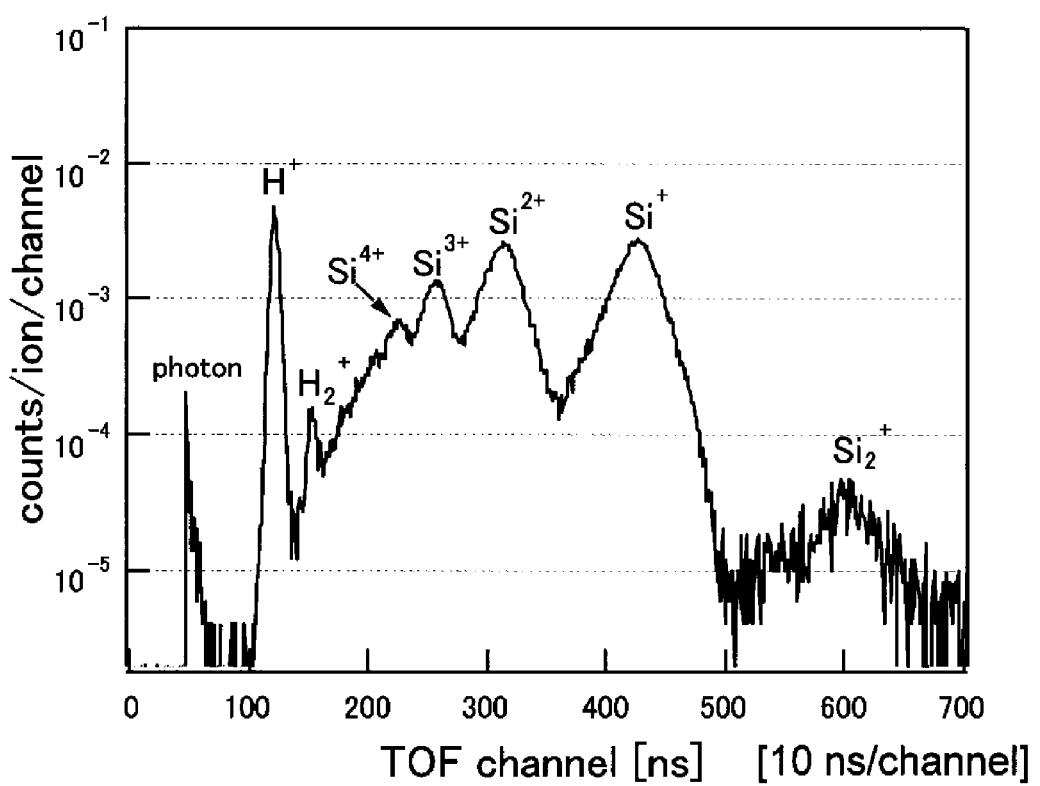

SURFACE ANALYZER OF OBJECT TO BE MEASURED AND ANALYZING METHOD

TECHNICAL FIELD

The present invention relates to an apparatus and method to analyze an atom and so on absorbed on a surface of an object to be measured like semiconductor substrate using multicharged ions as ion source.

BACKGROUND ART

Removing an electron from an atom forms a positive ion. Positive ions produced in this way are used for various processing units and analyzers such as impurity ion implantation equipment used for manufacturing semiconductor devices and dry etching equipment using plasma discharge involving ions and electrons. Ion implantation equipment turns n- or p-type impurities into positive ions to implant impurity ions of a given amount into the doping region of a semiconductor substrate of a semiconductor device.

By the way, that which has more than two electrons removed, such as, e.g., $Xe^{44+}$ ion, is called a positive multicharged ion, which has an extremely large internal energy. It is known that bombarding multicharged ions on a solid surface causes many peculiar phenomena such as emission of a large number of secondary electrons (see Non Patent Literature 1 in the list below) and giving rise to a large structural change in nanometer size around a point of incidence of the multicharged ions (see Non Patent Literature 2 in the list below).

Unique interactions of such multicharged ions with a material have focused the spotlight of attention upon their feasible application to processes in a nanometer region such as single-ion implantation and fabrication of a quantum dot (see Non Patent Literature 3 in the list below).

As the ion source from which to produce such multicharged ions there are generally known electron cyclotron resonance (ECR) type ions generating source (ECRIS) and electron beam type ions generating source (EBIS), the latter being featured by high degree of ionization of ions obtained.

As an EBIS there is known an apparatus of the National Institute for Fusion Science that has been developed for researches in the atomic physics (see, e. g., Non Patent Literature 4 in the list below). This apparatus comprises an electron source (cathode), a drift tube, a collector, a solenoid magnet and an ion extracting lens so configured that electrons exiting the cathode are passed through the drift tube and collected by the collector. The electrons are compressed by a strong magnetic field formed in the drift tube, becoming an electron beam of large current density. On the other hand, a gas introduced from the vicinity of the cathode becomes multicharged ions by impact ionization of electrons, because a square well potential is formed in the drift tube to be a barrier to ions.

In 1988 EBIT (electron beam ion trap) was developed which was improved over the EBIS (see Non Patent Literature 5 in the list below). The EBIT which is identical in principle of generating multicharged ions to the EBIS uses a superconducting Helmholtz type coil and a reduced length of the drift tube such as to avoid the instability of plasma in the drift tube, thereby improving the confinement time for ions so that the high multivalent multicharged ions can stably be retained. As a consequence, in the EBIT it has been made possible to squeeze an electron beam in the drift tube to the ultimate to form highly ionized ions.

As an EBIT there has also been developed by the present inventors an apparatus (see Non Patent Literature 6 in the list below) that has an electron accelerating voltage of 300 kV at its maximum to allow completely ionizing uranium (U). This EBIT was developed for researches in the atomic physics and has the highest performance in the world as the internal energy of multicharged ions that can be produced.

By the way, as a method of analysis using ions, secondary ion mass spectrometry (SIMS), which uses monovalent ions as a sputter source, is conventionally known.

Surface analysis using slow multicharged ions as a sputtering source described above was attempted (see Non Patent Literature 7). Non Patent Literature 7 discloses the detection of $H^+$ ions (protons) obtained when multicharged ions having a valence of 4 to 12 were irradiated onto the surface of Si at the speed as low as 2 keV to 5 keV.

CITATION LIST

Non Patent Literature

Non Patent Literature 1: J. W. McDonald, D. Schneider, M. W. Clark and D. DeWitt, Phys. Rev. Lett., Vol.68, (1992), p.2287

Non Patent Literature 2: T. Meguro et al., Appl. Phys. Lett., Vol.79, (2001), p.3866

Non Patent Literature 3: T. Schenkel et al., Appl. Phys., Vol.94, (2003), p.7017

Non Patent Literature 4: Nobuo Kobayashi, Shunsuke Oya and 7 others, Plasma Laboratory at Nagoya University, Data and Technical Report IPPJ—DT—84, 1981

Non Patent Literature 5: M. A. Levin and 7 others, Physica Scr., T22, 1988, p. 157

Non Patent Literature 6: Shunsuke Ohtani, Makoto Sakurai, The Journal of the Japan Society of Plasma Science and Nuclear Fusion Research, Vol.73, 1997, p.1063

Non Patent Literature 7: Yasunori Yamazaki The 52nd Spring Meeting, 2005, The Japan Society of Applied Physics and related societies, 29p-C-3, 2005

SUMMARY OF INVENTION

Technical Problem

As a conventional technique, the analytical method adaptable to light elements using multicharged ions having a valence of twelve or lower is known. However, since its detection sensitivity is low, it is difficult to analyze light elements such as hydrogen atoms attached to the surface of a solid, etc. in a short time. A period of time as long as approximately 12 hours is required to analyze light elements by this method. In addition, even if measurement is taken with the object to be measured maintained in ultrahigh vacuum state, it is difficult to obtain proper analysis results because residual gas in a vacuum tank or gas escaping from the inner wall of the vacuum chamber reattaches to the object to be measured.

In addition, when analyzing an object made of compound using a conventional secondary ion mass spectrometer, which uses monovalent ions as a sputtering source, it is difficult to obtain secondary ion intensity reflecting the stoichiometric composition of the compound, because of the difference in the ionization rate of the particles sputtered from the surface of the object to be measured, namely secondary ions.

In view of the problems described above, a purpose of the present invention is to provide an analyzer and an analyzing method which are capable of efficiently detecting atoms and molecules existing on or near the surface of an object to be measured using multicharged ions, namely multivalent ions.

Solution to Problem

To achieve the above objective, an analyzer for analyzing a surface of an object to be measured according to the present invention comprises: a stage for placing an object to be measured; a source for generating multicharged ions for irradiating a beam of multicharged ions having a valence of 15 or higher to the object to be measured placed on the stage; a mass analyzer for detecting secondary ions generated as a result of irradiating a beam of multicharged ions to the object to be measured; a secondary electron detector for detecting secondary electrons generated as a result of irradiating the beam of multicharged ions to the object to be measured; and a controller of mass analyzer for generating analysis start signals in response to the secondary electron signals received, and transmitting the start signals to the mass analyzer.

In the above configuration, the secondary electron detector preferably has two or more pieces of secondary electron detecting apparatus electronically isolated from each other. The secondary electron detecting apparatus preferably comprises two or more pieces of Channeltron or micro-channel plate having two or more anode electrodes.

The source for generating multicharged ions preferably has a multicharged ion guide, into one end of which the beam of multicharged ions from the source for generating multicharged ions enters, and from the other end of which the beam of multicharged ions goes out, and the other end of the source for generating multicharged ions is of a capillary structure.

According to the above configuration, by irradiating a beam of multicharged ions having a valence of 15 or higher onto the surface of the object to be measured, elements having a light mass such as $H^+$, which can hardly be analyzed using other methods, can be measured highly sensitively and in a short time. For example, elements having a light mass such as hydrogen attached onto the surface of a silicon (Si) semiconductor substrate, for example, can be measured quantitatively, which is useful for assessing substrate cleaning process, etc. in semiconductor manufacturing process.

The method of analyzing the surface of an object to be measured according to the present invention comprises: a step of irradiating a beam of multicharged ions with their valence changed within the range 15 or higher; and a step of assessing a relation between a valance of the beam of multicharged ions and a count of the secondary ions generated from specific elements on the surface of the object to be measured to determine a valence of a beam of multicharged ions for the specific elements.

In the above configuration, the object to be measured preferably comprises two or more constituent elements, and a relation between a valance of the beam of multicharged ions and a count of secondary ions generated from each constituent element is assessed to determine a valence of multicharged ions yielding a composition ratio of each constituent element.

According to the above configuration, by irradiating an optimum beam of multicharged ions having a valence of 15 or higher to the element to be detected on the surface of the object to be measured, elements having a light mass such as $H^+$, which can hardly be analyzed using other methods, can be measured quantitatively, highly sensitively, and in a short time.

Advantageous Effects of Invention

According to the present invention, since secondary ion signals generated by irradiating a beam of multicharged ions having a valence of 15 or higher to the object to be measured increase in proportion to the exponential of the valence, 4th power of the valence for example, the surface of the object to be measured can be analyzed in a short time, and objects that have undergone surface cleaning can also be analyzed highly accurately because no reattachment of residual gas, etc. occurs.

BRIEF DESCRIPTION OF DRAWINGS

FIG. 8 is a profile of analysis example 1 obtained by TOF-SIMS.

FIG. 10 is a profile of analysis example 3 obtained by TOF-SIMS.

DESCRIPTION OF EMBODIMENTS

Figure 1:
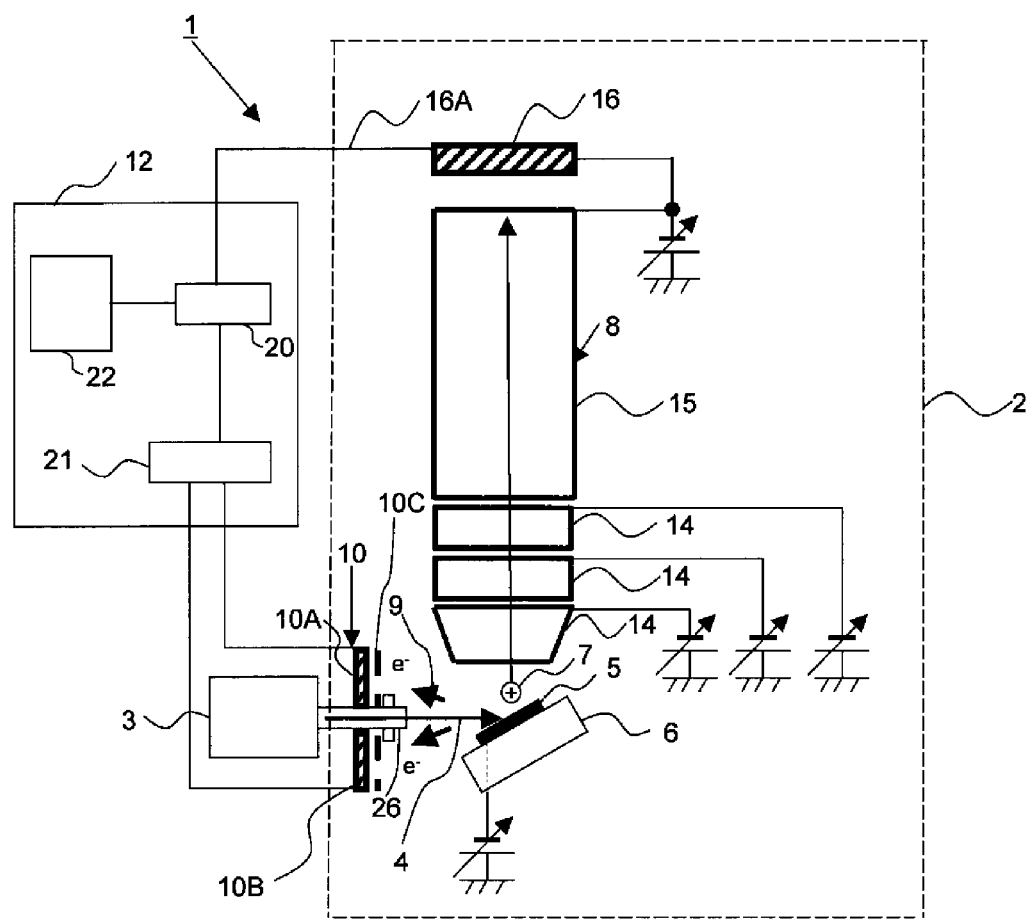
FIG. 1 is a cross sectional view diagrammatically illustrating the structure of a surface analyzer for analyzing the surface of an object to be measured using multicharged ions according to the present invention.

The present invention will hereinafter be described in detail based on the embodiment shown in the drawings.

FIG. 1 is a cross sectional view diagrammatically illustrating the structure of a surface analyzer 1 for analyzing the surface of an object to be measured using multicharged ions according to the present invention. The surface analyzer 1 using multicharged ions according to the present invention shown in FIG. 1 comprises a stage 6 for placing an object to be measured 5, a source for generating multicharged ions 3 for irradiating a beam of multicharged ions 4 having a valence of 15 or higher to the object to be measured 5 place on the stage 6, a mass analyzer 8 for detecting secondary ions 7 generated as a result of irradiating the beam of multicharged ions 4 to the object to be measured 5, a secondary electron detector 10 for detecting secondary electrons 9 generated by irradiating the beam of multicharged ions 4 to the object to be measured 5, and a controller of mass analyzer 12 for generating analysis start signals in response to the secondary electron detection signals from the secondary electron detector 10 received, and transmitting the signals to the mass analyzer 8.

The source for generating multicharged ions 3 is connected to a vacuum chamber 2, in which the stage 6, mass analyzer 8, and secondary electron detector 10 are installed, and the controller of mass analyzer 12 is installed outside the vacuum chamber 2. The vacuum chamber 2 may be evacuated by a vacuum pumping device (not shown), independent of the vacuum pumping device of the source for generating multicharged ions 3, which will be described later.

The mass analyzer 8 of this embodiment is a time of flight (TOF) type mass analyzer comprising a lens 14, a flight tube 15 and a secondary ion detecting apparatus 16 for detecting a secondary ion 7, but the mass analyzer 8 can adopt various other systems.

The controller of mass analyzer 12 comprises a multichannel analyzer 20 for detecting signals from the secondary ion detecting apparatus 16 by time of flight, an analysis start signal generating means 21 for detecting the time when the beam of multicharged ions 4 enters the object to be measured 5 and transmitting it to the multi-channel analyzer 20, and a computer 22 for processing the signals from the multi-channel analyzer 20.

The surface analyzer 1 using multicharged ions according to the present invention differs from conventional mass analyzers in that
(1) it uses multicharged ions having valence of 15 or higher, whereas conventional mass analyzers irradiate monovalent ions to the object to be measured, and
(2) secondary ions 7 generated from the object to be measured 5 to which multicharged ions are irradiated are detected by the mass analyzer 8 and the controller of mass analyzer 12.

First, the source for generating multicharged ions 3 will be described in respect of (1) above. The source for generating multicharged ions 3 to be used for the present invention can be selected regardless of generating methods, on condition that multicharged ions having valence of 15 or higher can be generated.

Figure 2:
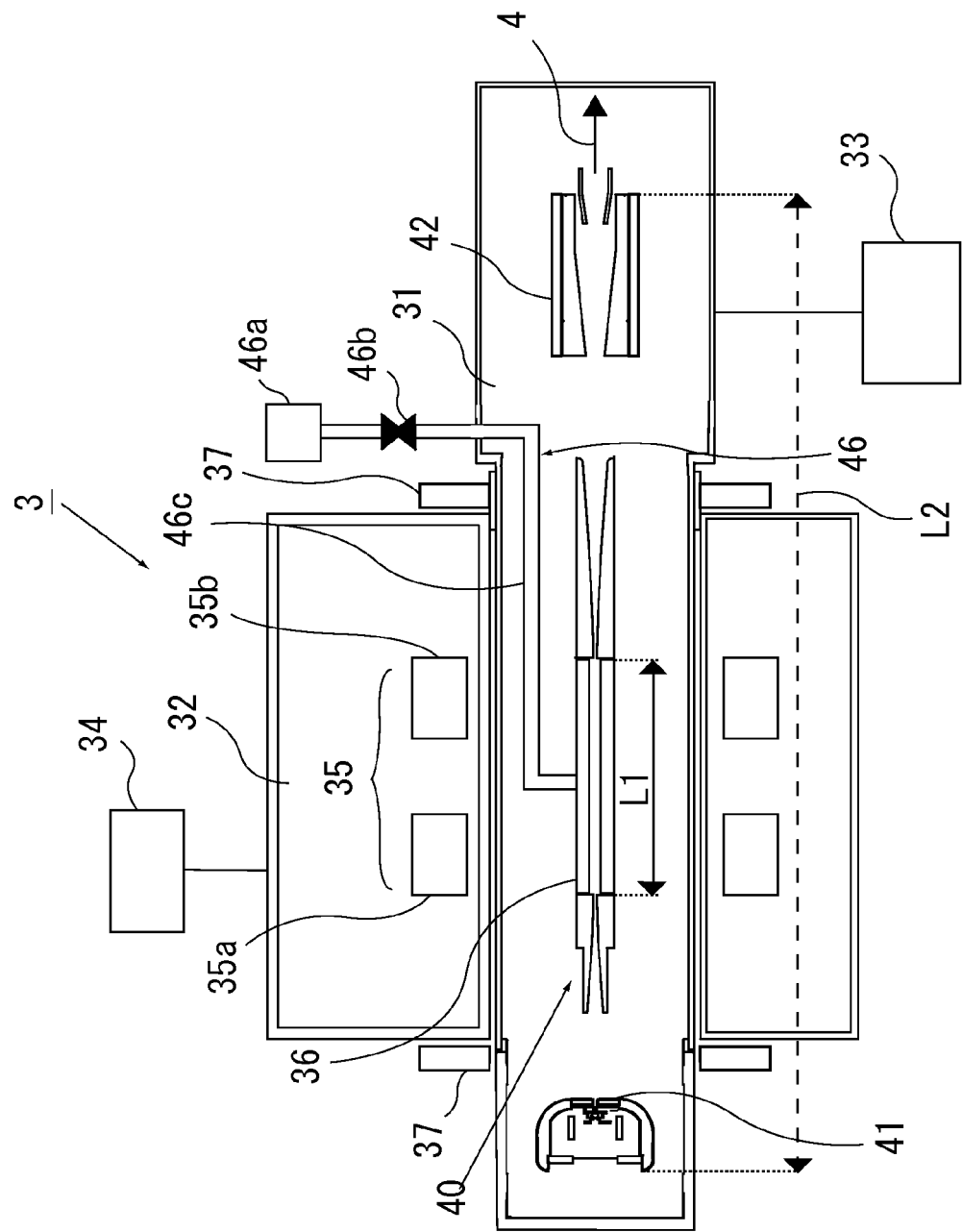
FIG. 2 is a cross sectional view diagrammatically illustrating the structure of a source for generating multicharged ions.

FIG. 2 is a cross sectional view diagrammatically illustrating the structure of a source for generating multicharged ions 3. In the source for generating multicharged ions 3, a first and the second vacuum chambers 31 and 32 are adapted to be evacuated, independently of each other, by vacuum pumping units 33 and 34, respectively. The interior of the first vacuum chamber 31 is made at an extremely high vacuum of $1 \times 10^{-5}$ Pa (Pascal) or less, especially of $1 \times 10^{-9}$ Pa or less for generating multicharged ions. For example, a vacuum of $10^{-10}$ Pa ($10^{-12}$ Torr) is required for generating $U^{92+}$. Accordingly, the first vacuum chamber 31 is provided with a baking means using such as a baking heater (not shown) for degassing. The use of such a baking means allows the first vacuum chamber 31 to be baked to an extent of 250° C. to 300° C.

Here, the first and the second vacuum chambers 31 and 32 are composed at least along their opposing surfaces of a nonmagnetic material so that a magnetic field from the superconducting magnet 35 can be applied to the drift tube 36. The nonmagnetic material used may be austenitic stainless steel (e.g., SUS-304 or SUS-316) or aluminum.

The superconducting magnet 35 is received in the second vacuum chamber 32 so that it is thermally isolated from the exterior. The superconducting magnet 35 is cooled at a very low temperature, e.g., of 10 K (−263° C.). This second vacuum chamber 32 is held at a high degree of vacuum around $10^{-4}$ Pa. To obtain such a high vacuum, the baking means is unnecessary. The second vacuum chamber 32 is provided on a peripheral area of the first vacuum chamber 31 with a magnetic shield 37, which is disposed so that the magnetic field from the superconducting magnet 35 may not come through the electron source 41 or a portion of the drift tube 36 on the side of the collector 42 of the ion source electrode 40. This magnetic shield 37 used may be made of a ferromagnetic material such as soft iron.

Figure 3:
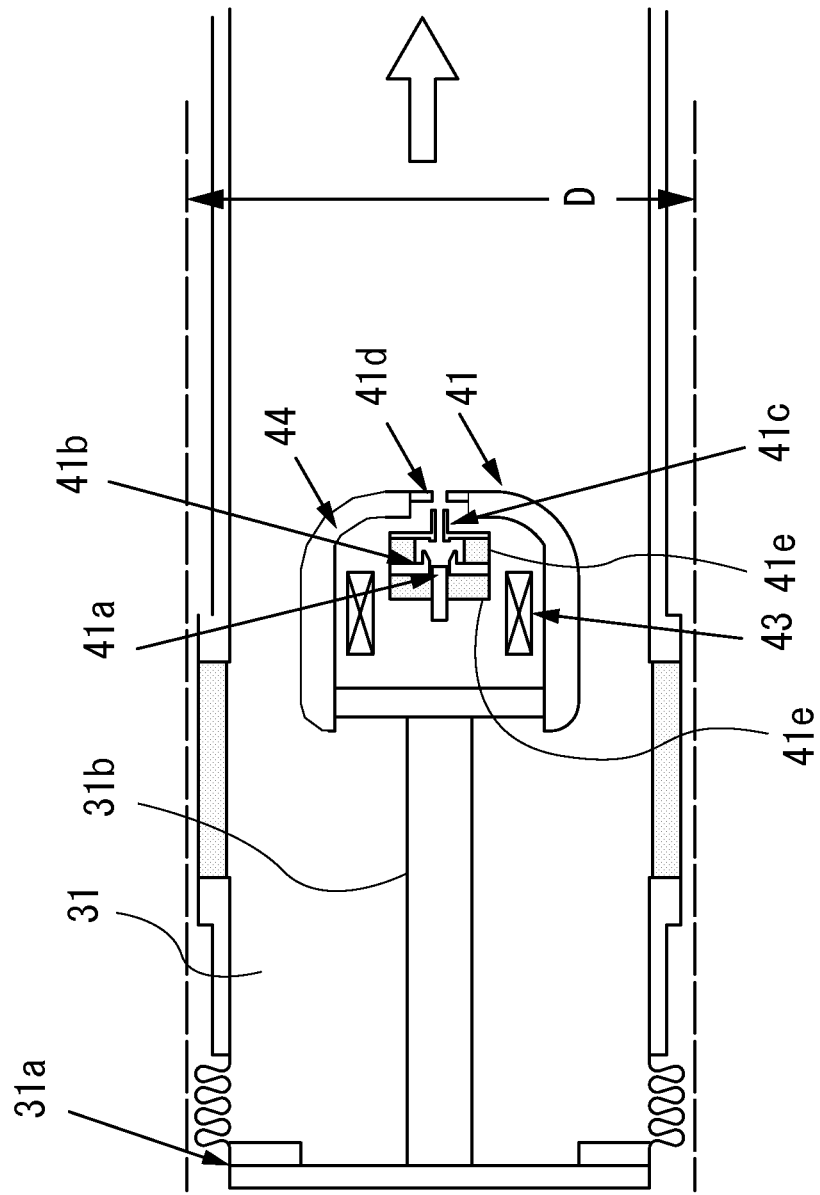
FIG. 3 is an enlarged cross-sectional view diagrammatically illustrating the structure of the electron source shown in FIG. 2.

FIG. 3 is an enlarged cross sectional view diagrammatically illustrating the structure of the electron source 41 shown in FIG. 2. As shown, the electron source 41 is supported on a support arm 31b by an ultrahigh vacuum flange 31a at a left side face of the first vacuum chamber 31 so that it lies on a horizontal, central axis of the first vacuum chamber 31. The superconducting magnet 35 received in the second vacuum chamber 32 has a bore whose diameter is indicated by D. The arrows in the Figure indicate a course of evacuation. The electron source 41 has a filament (cathode) electrode 41a, a focus electrode 41b, an anode electrode 41c and a snout electrode 41d arranged from the left to the right hand side as shown, each of which is insulated by an electrical porcelain 41e, 41e. The electron source 41 is provided with a bucking coil 43 to make the magnetic field in the vicinity of the cathode zero and it is received in a region of the magnetic shield 44.

Here, as shown in FIG. 2, an electron beam produced from the electron source 41 needs to be guided towards the collector 42 without striking on the drift tube 36. To this end, the cathode, anode and snout electrodes 41a, 41c and 41d are fitted with the electrical porcelains 41e and 41e and assembled together so that their axes are made coincident with one another with high precision.

As an example, in drawing a current of 300 mA from the cathode electrode 41a, the anode electrode 41c and the snout electrode 41d are given +10 kV and +15 kV, respectively, based on a filament potential. While a high voltage of +15 kV at maximum is applied to the bucking coil 43 and the magnetic shield 44 as well as to each electrode, making each of the parts small while ensuring their mutual insulation allows limiting a region of the magnetic shield 44 to a diameter of 100 mm. It is then possible to accommodate the electron source 41 in the ultrahigh vacuum flange 31a having an outer diameter of 162 mm and an inner diameter of 102 mm and to limit the second vacuum chamber 32 at the side of the electron source 41 to a diameter of 152 mm. Since the inner diameter of the ultrahigh vacuum flange 31a is much larger than the diameters of the magnetic shield 44 and the drift tube 36, the gas emitted from a region of the electron source 41 can be evacuated efficiently. Thus, making the electron source 41 smaller in size allows making smaller the annular bore of the second vacuum chamber 32 accommodating the superconducting magnet 35, namely the bore diameter of the superconducting magnet 35.

The drift tube 36 is made up of several divided cylindrical electrodes and has an electric field configured so that its both ends create a barrier (square well potential) to ions.

A gas becoming ions is introduced by a gas ion infeed means 46 from side faces of the drift tube 36 into its inside. The gas ion infeed means 46 comprises a gas source 46a, a flow controller 46b and a piping 46c etc. into the first vacuum chamber 31.

Figure 4:
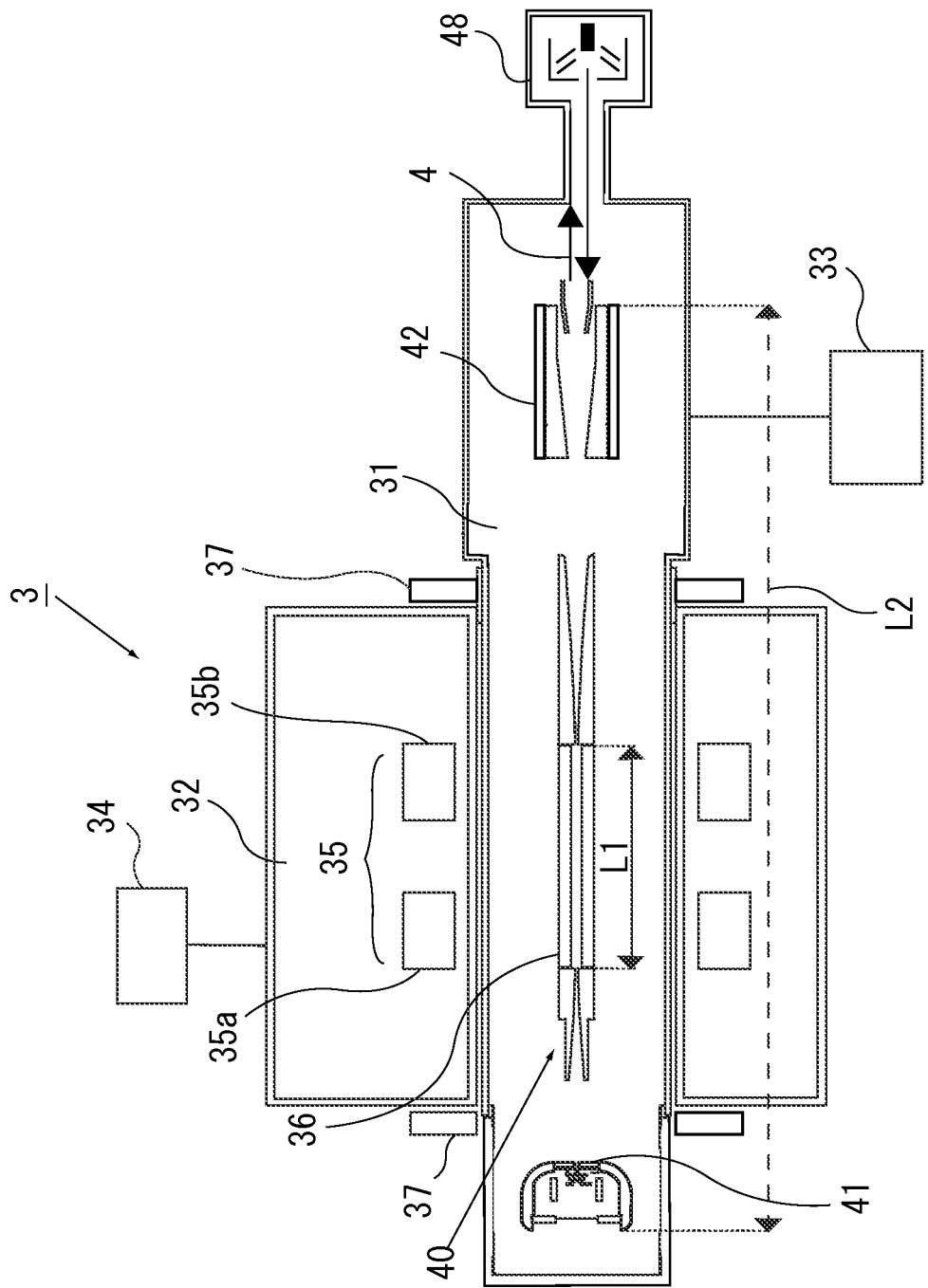
FIG. 4 is a cross sectional view diagrammatically illustrating the structure of a multicharged ions generating source having a solid ion source as its ion source.

On the other hand, if solid ions are to be generated as its source, a solid ion source may be used. FIG. 4 is a cross sectional view diagrammatically illustrating the structure of a multicharged ions generating source 3 having a solid ion source as its ion source. The multicharged ions generating source 3 shown in FIG. 4 differs from that shown in FIG. 2 in that in place of the gas ion infeed means 46, a solid ion infeed means 48 is provided at a right hand side of the collector 42. The solid ion infeed means 48 may use a vacuum arc type ion source which is in the form of a needle of a solid material subjected to vacuum arc discharge for generating monovalent ion to generate desired ions. Ions produced from the solid ion infeed means 48 and entering the first vacuum chamber 31 are passed through the collector 42 and then injected into the drift tube 36.

Ions injected into the drift tube 36 from the ion infeed means constituted by either the gas ion infeed means 46 or the solid ion infeed means 48 are trapped in the square well potential for a given time period, progressed their impact ionization by electrons and they become multicharged ions. Of such multicharged ions, those which by collisions with electrons are elevated in kinetic energy so as to cross the barrier, are taken out of the multicharged ions generating source 3. When the degree of ionization for ions reaches the ultimate or a state that continuing electrons to strike no longer causes ionization to proceed, the configuration of electric field is altered so as to cause multicharged ions to issue out, thereby producing a beam of multicharged ions 4.

The collector 42 is an electrode for collecting electrons passing through the drift tube 36 and it may be made of electrodes such as a suppressor, collector or extractor electrode etc. The cathode electrode 41a and the collector 42 have a voltage of minus several tens kV to minus 300 kV at the maximum applied thereto relative to the earth. Such an accelerating voltage may suffice to be a voltage by which desired multicharged ions are obtained. Electrons have a maximum accelerating voltage applied thereto immediately before they are incident on the drift tube 36 and those past the drift tube 36 are decelerated to around 2 to 3 kV ahead of the collector 42 and collected by the collector 42. Accordingly, the collector 42 has absorbed an electric power that is a product of this voltage and a consequent electron beam current. This electric power becomes 900 W when the voltage ahead of the collector 42 is 3 kV and the electron beam current is 300 mA. If electrons in a pinched state impinge on the collector 42, a collector portion impinged on will be molten. Thus, the collector 42 is designed to have an electrode structure that can be cooled by a coolant such as to collect electrons while expanding a beam thereof.

Mention is next made of the superconducting magnet 35.

As shown in FIGS. 2 and 4, the superconducting magnet 35 makes use of a so-called Helmholtz coil that consists of a first coil portion 35a and a second coil portion 35b. If the first and the second coil portions 35a and 35b are assumed to have a radius 'a' and to be spaced apart by a distance 'a' that is the same as radius 'a', the magnetic field in the central region of the juxtaposed coil portions can be made even. Here, the superconducting magnet 35 is cooled to be a superconducting state by a cryostat or closed-cycle refrigerator using He as its coolant.

A feature of the multicharged ions generating source 3 is that the superconducting magnet 35 for ion trapping is received in the second vacuum chamber 32 and the first vacuum chamber 31 is disposed to pass through an annular or ring-shaped bore of the second vacuum chamber 32. In other words, the first vacuum chamber 31 is passed through a bore of the superconducting magnet 35. As mentioned before, the ion source electrode 40 comprising the electron source 41, the drift tube 36 and the collector 42 is disposed in the first vacuum chamber 31. The second vacuum chamber 32 in which the superconducting magnet 35 is accommodated is made removable from the first vacuum chamber 31 without breaking vacuum of both the chambers. Therefore it is sufficient if the first vacuum chamber 31 is made in which the ion source electrode 40 is accommodated therein, and the manufacture is easy since the superconducting magnet 35 used can be a product on the consumer market. Consequently, in the multicharged ions generating source 3 according to the present invention, the superconducting magnet 35 and the ion source electrode 40 need not be made precisely in an integrated structure as in the conventional multicharged ions generating source.

Mention is next made of an operation of the multicharged ions generating source used for the present invention constructed as mentioned above.

Figure 5:
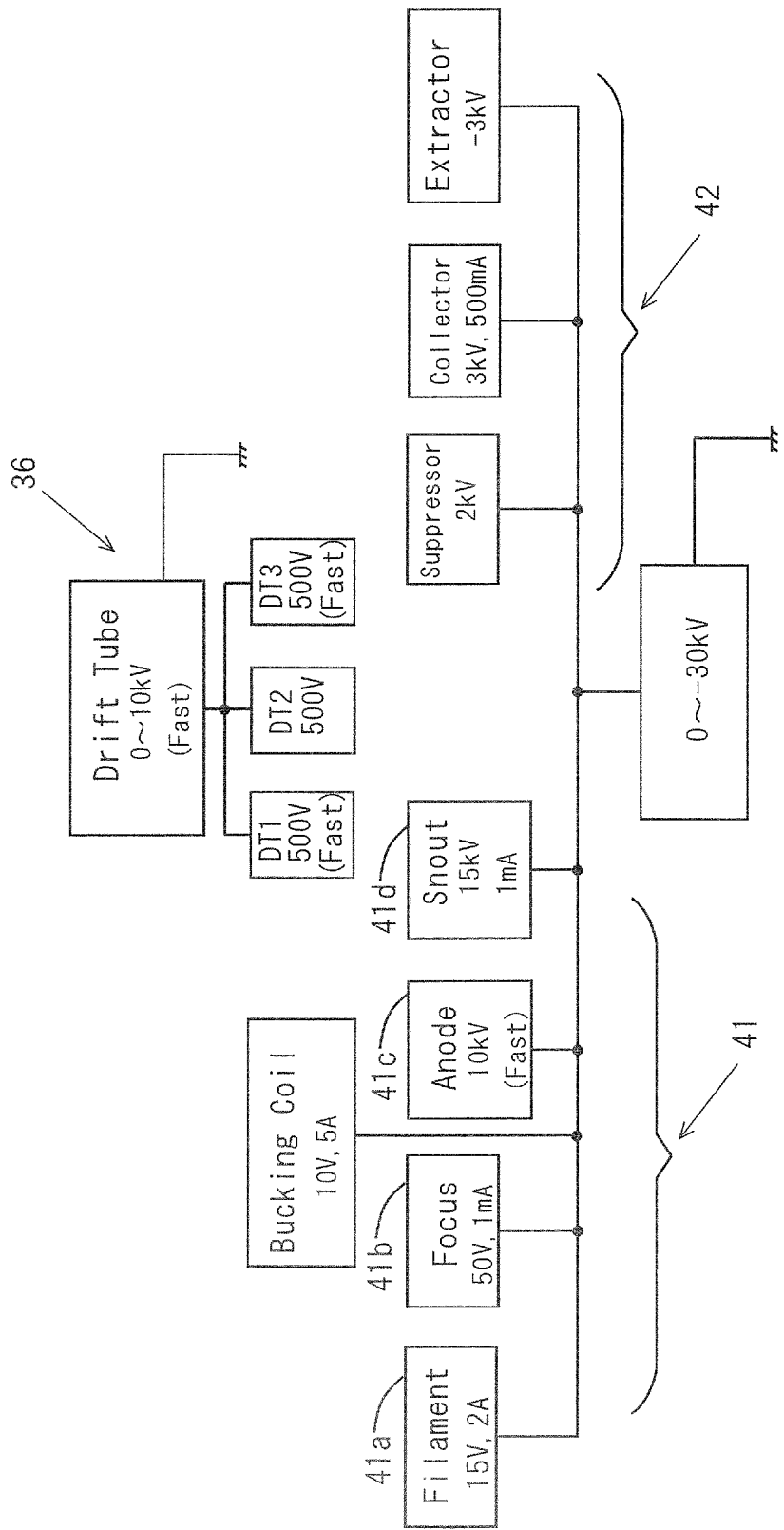
FIG. 5 is a typical block diagram for the illustration of a power supply whose output is applied to a multicharged ions generating source.

FIG. 5 is a typical block diagram for the illustration of a power supply whose output is applied to a multicharged ions generating source 3. There is shown an example in which the electron accelerating voltage is 40 kV. As shown, the filament, focus, anode and snout electrodes 41a, 41b, 41c, 41d in the electron source 41 are supplied from power sources of 15 V and 2A, 50 V and 1 mA, 10 kV, and 15 kV and 1 mA, respectively, each superimposed to a power source of −30 kV. And, as for the drift tube 36, its first, second and third electrodes are each supplied with 500 V superimposed to a power source of 10 kV.

Further, the suppressor, collector and extractor electrodes of the collector 42 are supplied from power supplies of 2 kV, 3 kV and 500 mA and −3 kV, respectively, superimposed to −30 kV of a power supply.

As mentioned above, electrons generated from the electron source 41 are passed through the drift tube 36 disposed in a magnetic field produced by the superconducting magnet 35. When the power supply shown in FIG. 5 is used, electrons are accelerated to 40 kV at the maximum between the electron source 41 and the drift tube 36. The electrons accelerated and incident in the drift tube 36 is compressed by the strong magnetic field built up in the drift tube 36 by the superconducting magnet 35, forming an electron beam having a high current density (up to 1000 A/cm$^2$) which is collected into the collector 42. If the power supply shown in FIG. 5 is used, the electron beam is decelerated to around 2 to 3 kV and then collected into the collector 42. In this case, the electrons are designed to have a maximum accelerating voltage applied thereto immediately ahead of the drift tube 36. Since to ionize an atom, the atom must be bombarded with an electron having an energy more than the ionization energy of a bound electron, completely ionizing a heavy element, e.g., xenon (Xe), entails an energy higher than the ionization energy of the is orbital (i.e., 35 keV for Xe), thus necessitating an accelerating voltage more than 35 kV.

On the other hand, the gas introduced from the gas infeed means 46 to be ionized, is ionized in the drift tube 36. Where the drift tube 36 has several divided electrodes, those constituting its both ends are given a potential such as to form a barrier (square well potential) to ions. Ions are trapped in the square well potential for a given time period in which ionization of gas atoms repetitively bombarded with an electron beam is advanced. Their impact ionization by electrons proceeds until they become multicharged ions 4. Multicharged ions that are elevated in kinetic energy so as to cross the barrier by being bombarded with electrons are taken out of the source for generating multicharged ions 3. When the degree of ionization for ions thus reaches the ultimate or a state that continuing electrons to impinge no longer causes ionization to proceed, the configuration of electric field is altered so as to cause multicharged ions to issue out, thereby producing a beam of multicharged ions 4.

When multicharged ions produced with the drift tube 36 are drawn out of the drift tube 36, they are once accelerated to 40 kV between the drift tube 36 and the collector 42, and when issuing from the first vacuum chamber 31 which is at the earth potential they are decelerated down to 10 kV to exit.

The intensity of a multicharged ions beam 4 obtained is proportional to the length L1 (see FIG. 2) of the ion trapping drift tube 36 and the emission current whereas the time period until the degree of ionization reaches the ultimate is proportional to the current density of electrons. By the way, if the length of the drift tube 36 is too long, the plasma becomes unstable, and the multicharged ions of high degree of ionization cannot be formed.

Also, the current density of an electron beam becomes higher, but not proportionally, as the strength of a magnetic field applied by the superconducting magnet 35 to the drift tube 36 is higher. For this reason, the intensity of a multicharged ions beam 4 obtained per unit time can be made higher as the electron beam current density is higher and the trapping region is longer in length.

The mechanism of multicharged ions generation 3 is the same as those of the conventional multicharged ions generating source.

A feature of the multicharged ions generating source 3 in the present embodiment is that a vacuum pumping unit 33 for the first vacuum chamber 31 containing the ion source electrode 40 and a vacuum pumping unit 34 for the second vacuum chamber 32 receiving the superconducting magnet 35 can be removed and separated from each other. Thus, in the state that the second vacuum chamber 32 containing the superconducting magnet 35 is separated from the first vacuum chamber 31, it is possible to sufficiently heat and degas the first vacuum chamber 31 and the ion source electrode 40 housed in the first vacuum chamber 31. Therefore, it is possible to evacuate the first vacuum chamber 31 for producing multicharged ions in a short period of time to an extremely high vacuum. For example, if an electron beam by error impinges on the drift tube 36, then only the first vacuum chamber 31 accommodating the ion source electrode 40 may be mended in the multicharged ions generating source 3.

Since this allows the vacuum to be quickly built up in a region of the ion source electrode 40 of the multicharged ions generating source 3, it is possible to realize a multicharged ions generating source 3 which is excellent in operability and maintainability.

The stage for object 6 may be made movable so that its position can be controlled. An XYZ stage can be used as the stage for object 6, for example. A piezoelectric element or a step motor can be used to drive the XYZ stage 6 in the XYA direction.

The mass analyzer 8 for detecting secondary ions 7 generated from the object to be measured 5 to which a beam of multicharged ions 4 is irradiated, and the controller of mass analyzer 12 will hereinafter be described in detail in respect of (2) above. If a pulsed beam of multicharged ions 4 is irradiated to the object to be measured 5, secondary ions 7 and secondary electrons 9 are generated from the elements existing on the surface of the object to be measured 5. The secondary ions 7 generated are collected via a lens 14, enters a flight tube 15, and after the elapse of flight time determined by the mass, etc. of the secondary ions 7, enters the secondary ion detecting apparatus 16.

Meanwhile, the secondary electrons 9 generated as a result of irradiating a beam of multicharged ions 4 onto the object to be measured 5 are detected by a secondary electron detector 10. In this case, since several dozen to several hundred secondary electrons 9 are generated as a result of irradiating single multicharged ion 4, the number of irradiated beams of multicharged ions 4 can be measured accurately. As the secondary electron detector 10, it is preferable to use a secondary electron detecting apparatus 10A, etc. ensuring highly sensitive detection of secondary electrons 9 generated when single multicharged ion 4 is irradiated to the object to be measured 5.

The secondary electron detector 10 shown in FIG. 1 is placed on a plane orthogonal to the direction of travel of the beam of multicharged ions 4 entering the object to be measured 5, with one each 10A and 10B placed at the top and the bottom respectively. As shown by the figure, a lens such as a grid 10C having a lens function for collecting secondary electrons 9 may be provided between the secondary electron detector 10 and the object to be measured 5. To double the number of secondary electrons generated, a shield can also be provided to prevent voltage to be applied to the secondary electron detecting apparatus 10A from leaking outside. The shield may be made of a metal and in a shape enclosing the secondary electron detecting apparatus 10A and 10B.

The analysis start signal generating means 21 for transmitting analysis start signals to the multichannel analyzer 20 receives the output from the secondary electron detector 10 and processes measurement data. Generally, since secondary electron signals have much noise, measurement errors may occur. To eliminate measurement errors due to generated noise, the secondary electron detector 10 may comprise two pieces of secondary electron detecting apparatus 10A and 10B electrically isolated from each other as shown above.

If two or more pieces of secondary electron detecting apparatus 10A and 10B are provided, the analysis start signal generating means 21 may be equipped with a circuit for judging whether two or more pieces of measurement data on secondary electrons 9 generated form the object to be measured 5 coincide with each other. The judgment circuit can judge that the measurement data is correct when two or more pieces of measurement data of the secondary electron detecting apparatus 10A and 10B coincide with each other. Since many secondary electrons 9 are discharged when a beam of multicharged ions 4 is irradiated, by assuming that signals are correct only when those obtained from at least two pieces of secondary electron detecting apparatus 10A and 10B coincide with each other, the number of ions can be measured accurately.

FIG. 6(A) is a schematic diagram illustrating the configuration of the analysis start signal generating means 21, and FIG. 6(B) is a truth table of the AND circuit 24 used by the analysis start signal generating means 21.

As shown in FIG. 6(A), the analysis start signal generating means 21 is equipped with an AND circuit 24, etc. for performing logical AND operation as a judgment circuit. To its inputs 24A and 24B, the outputs of the two pieces of secondary electron detecting apparatus 10A and 10B are connected. The output of the secondary electron detecting apparatus 10A and 10B has been subjected to signal processing so that high-level and low-level signals of the AND circuit 24 are output via an amplifier (not shown). As the secondary electron detecting apparatus 10A, a so-called photomultiplier capable of detecting secondary electrons 9 can be used. As the secondary electron detecting apparatus 10A having such multiplying effect, two or more pieces of Channeltron can be used or a micro-channel plate having anode electrodes can be used.

Figure 6:
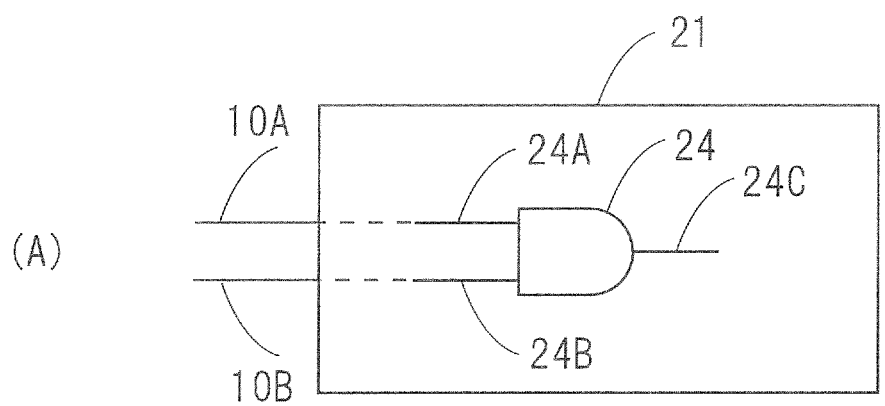
FIG. 6(A) is a schematic diagram illustrating the configuration of the analysis start signal generating means.
FIG. 6(B) is a truth table of the AND circuit used by the analysis start signal generating means.

The secondary electron detecting apparatus 10A and 10B shown in FIG. 6 transmit a high-level signal, namely signal 1, to the AND circuit 24, when secondary electrons 9 generated by one multicharged ion are detected. Reversely, a low-level signal, signal 0, is transmitted to the AND circuit 24 when secondary electrons 9 are not detected. Consequently, as shown by the truth table of the AND circuit 24 shown in FIG. 6(B), in the AND circuit 24, when both of the two inputs 24A and 24B are 1, the output 24C becomes 1. The output 24C becomes 0 in all other cases. In other words, when the two pieces of secondary electron apparatus 10A and 10B both detect secondary electrons generated from one multicharged ion, the AND circuit judges that a multicharged ion has been generated. According to the judgment circuit adopting the AND circuit 24, even if the intensity of the multicharged ions entering the object to be measured 5 is extremely weak, such as the case where the pulse frequency of the multicharged ions is 1 Hz or lower, generation of multicharged ions can be detected.

The judgment circuit using AND circuit 24 with 2 inputs was described above. When using 3 or more pieces of secondary electron detecting apparatus to increase accuracy, an AND circuit 24 equipped with the number of inputs equivalent to the number of pieces of secondary electron detecting apparatus may be used. As a result, since a beam of multicharged ions 4 is judged to have been irradiated when the measurement data of the plurality of secondary electron detecting apparatus coincides with each other, noise can be removed and accuracy can be improved.

If the pulse frequency of the multicharged ions is 100 Hz or higher, the above judgment circuit 24 may be configured with the signals from the secondary electron detector 10 amplified with a high-speed amplifier, and the amplified signals may be input into the multichannel analyzer 20 via a timing discriminator.

The surface analyzer 1 in this embodiment is configured as described above. The operation of the surface analyzer 1 will be described below. A beam of multicharged ions 4 generated from the source for generating multicharged ions 3 is irradiated to the object to be measured 5. In this case, the irradiation position of the beam of multicharged ions 4 to the object to be measured 5 is controlled with a movable stage 6.

When the position of the object to be measured 5 is determined and then the beam of multicharged ions 4 is irradiated to the object to be measured 5, secondary ions 7 are generated from the atoms existing at the specified position of the object to be measured 5. The secondary electrons 9 generated in this case are detected by the secondary electron detecting apparatus 10A and 10B. The existence or non-existence of detected secondary electrons is judged by the analysis start signal generating means 21. Consequently, the output from AND circuit 24 in the analysis start signal generating means 21 being at a high level means that a beam of multicharged ions 4 is being irradiated to the object to be measured 5.

If the mass analyzer 8 is a TOF-type mass analyzing apparatus, the time when the output 24C of the AND circuit to be input to the controller of mass analyzer 12 becomes high level is defined as the measurement start time, and let this signal be called as the start signal of mass analysis measurement. Signals from the secondary ion detecting apparatus 16 in the TOF-type mass analyzer 8 obtained after the start signal is issued are those from the secondary ions 7 generated from the object to be measured 5. When the detection of signals of secondary ions 7 is completed, measurement stop signal 16A is transmitted from the secondary ion detecting apparatus 16 to the controller of mass analyzer 12.

Consequently, by analyzing the signals from the above start signal to the measurement stop signal 16A, mass analysis of the atoms existing at a given position of the object to be measured 5 can be performed.

With the surface analyzer 1 of the object to be measured according to the present invention, by using a beam of multicharged ions 4 having a valence of 15 or higher, secondary ions 7 can be generated from the object to be measured 5 in a short time, and sputtering efficiency can be enhanced significantly. According to the surface analyzer 1 of the present invention, since the secondary ion 7 signals generated from the object to be measured 5 as a result of irradiating the beam of multicharged ions 4 having valence of 15 or higher increase in proportion to the exponential of the valence, 4th power of the valence for example, the surface of the object to be measured can be analyzed in a short time. As a result, highly accurate analysis of objects to be measured 5 that have undergone surface cleaning can also be ensured without causing reattachment of residual gas, etc. to occur.

With the surface analyzer 1 according to the present invention, by irradiating a beam of multicharged ions 4 having a valence of 15 or higher onto the surface of the object to be measured 5, elements having a light mass such as $H^+$, which can be hardly measured by other methods, can be measured quantitatively, highly sensitively, and in a short time.

If the position of the object to be measured 5 is controlled using an XYZ stage 6 having a resolution on the order of nm, the spatial resolution can be enhanced considerably. With the enhanced spatial resolution, small amount of elements can be analyzed quantitatively, highly sensitively, and in a short period of time.

The above surface analyzer 1 may further comprise an equipment for observing the surface of the object to be measured 5. Such equipment includes an electron diffraction equipment, scanning electron microscope (SEM), etc.

With the surface analyzer 1 according to the present invention, the surface of various objects can be analyzed using a computer 22 based on the values detected by the multichannel analyzer 20.

Surface analysis examples will be described below.

(a) A pulse of single multicharged ion 4 having valence of 15 or higher is irradiated to the object to be measured 5, and measurement by pulse is repeated for a specified number of times.

(b) To eliminate measurement errors, pieces of data obtained by the measurement taken in (a) above are integrated using the computer 22, and when the average value converges to a certain value, irradiation of the beam of multicharged ions 4 is stopped.

According to the above analysis method, the surface of a single-element object 5 can be analyzed in a short time.

The method of analyzing the surface of an object to be measured 5 consisting of two elements, A and B, at the atomic ratio of x:y will hereunder be described. In this case, the chemical formula of the object to be measured is "$A_xB_y$."

(a) A pulse of single multicharged ion 4 having a valence of 15 is irradiated to the object to be measured 5, and measurement by pulse is repeated for a specified number of times.

(b) To eliminate measurement errors, the pieces of data obtained by the measurement taken in (a) above are integrated using the computer 22, and when the average value converges to a certain value, irradiation of the beam of multicharged ions 4 is stopped.

(c) A pulse of single multicharged ion 4 having a valence of 15 or higher (valence=15+n) is irradiated to the object to be measured 5, and measurement by pulse is repeated for a specified number of times.

(d) To eliminate measurement errors, the pieces of data obtained by the above repetitive measurement are integrated using the computer 22, and when the average value converges to a certain value, irradiation of the beam of multicharged ions 4 is stopped.

(e) The measurement described in (c) and (d) above is repeated to obtain data on a specified valence, up to 50 for example.
(f) From the above measurement data, the relation between the secondary ion 7 count of the constituent elements A and B and the valence of the beam of multicharged beams 4 is calculated. The valence that derives the count ratio (x:y) of the constituent elements A and B is found. The intensity of secondary ions reflecting stoichiometric composition of the object to be measured 5 expressed as AxBy can be obtained from this valence.
(g) If a valence reflecting the stoichiometric composition is obtained in step
(f) shown above, the beam of multicharged ions 4 having that valence is irradiated when an object 5 having the same composition is to be measured to allow surface analysis reflecting the stoichiometric composition to be conducted.

In the case in which the object to be measured 5 consists of 3 or more elements also, by finding the relation between the count and the valence of secondary ions 7 of the 3rd or subsequent elements such as C in the measurement described in (a) to (g), surface analysis can be conducted.

The method of surface analysis in the case in which the object to be measured 5 consists of two elements, A and B, and its composition is unknown will hereunder be described.

An object to be measured 5 whose atomic ratio (x:y) is known is used as a standard sample. A beam of multicharged ions 4 having a valence allowing the analysis reflecting the stoichiometric composition of the standard sample is irradiated to the object to be measured 5 whose composition is unknown, and measurement described in (a) and (b) is made to obtain the count of elements A and B. The obtained counts of elements A and B are defined as na and nb respectively. By comparing the counts na and nb of these elements, A and B, with the count of the standard sample, the composition of the object to be measured 5 having unknown composition can be found.

When the object to be measured 5 consists of 3 or more elements also, by finding the relation between the count of the secondary ions 7 of the 3rd and subsequent elements such as C and that of the standard sample, surface analysis can be conducted.

In the surface analyzer 1, a deceleration lens may be additionally installed between the source for generating multicharged ions 3 and the object to be measured 5. By installing a deceleration lens, the accelerating voltage of the beam of multicharged ions 4 irradiated from the source for generating multicharged ions 3 can be controlled. If the beam of multicharged ions 4 contains multivalent ions, an ion separator can also be additionally installed to select desired multivalent ions. As an ion separator, an analyzing magnet (bending magnet) or Wien filter using magnetic or electric field can be used.

Figure 7:
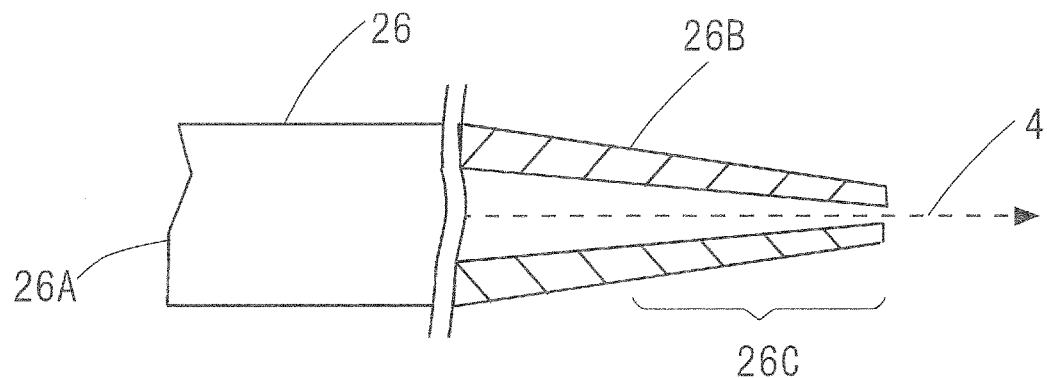
FIG. 7 is a cross-sectional view illustrating the structure of the tip portion of the multicharged ion guide shown in FIG. 1.

In the surface analyzer 1, a multicharged ion guide 26 may be additionally installed between the source for generating multicharged ions 3 and the object to be measured 5. FIG. 7 is a cross-sectional view illustrating the structure of the tip portion of the multicharged ion guide 26 shown in FIG. 1. A beam of multicharged ions 4 is irradiated from one end portion 26A of the multicharged ion guide 26, and the beam of multicharged ions 4 is discharged from the other end portion 26B. Namely, the multicharged ion guide 26 serves as a guide to lead the beam of multicharged ions 4 to the object to be measured 5, and the tip portion 26C on the other end portion 26B of the multicharged ion guide has an opening of approximately 100 nm or smaller in diameter, constituting a so-called capillary structure. This multicharged ion guide 26 is preferably made of an insulating material, and ceramics or quartz glass can be used. Such capillary structures can be produced by fusing a small tube made of quartz by heating, for example, and performing stretching processing in fused state.

Once the beam of multicharged ions 4 enters the multicharged ion guide 26, the internal wall of the multicharged ion guide 26 is charged. Consequently, in response to the repulsion of the internal wall of the multicharged ion guide 26, the beam of multicharged ions 4 travels along the central part of the multicharged ion guide 26, and enters the object to be measured 5 through the tip portion 26C of the capillary-structure. As a result, the diameter of the beam of multicharged ions 4 converges at the tip portion 26C of the multicharged ion guide 26, and then enters the object to be measured 5.

ANALYSIS EXAMPLE 1

Analysis examples using the surface analyzer 1 according to the present invention will hereinafter be described.

After the surface (100) of silicon (Si), which was the object to be measured 5, was heated at 1200° C. for 5 seconds three times, Xe ions having a valence of 50 ($Xe^{50+}$) was irradiated to the surface at the accelerating voltage of 3 keV. As secondary electron detecting apparatus 10A and 10B, Channeltron was used. Furthermore, to measure the beam of multicharged ions 4 irradiated to the object to be measured 5, another Channeltron was installed on the rear side of the object to be measured 5.

FIG. 8 is a profile of analysis example 1 obtained by TOF-SIMS. In FIG. 8, the horizontal axis represents the time of flight (ns), and the vertical axis represents the count of detected secondary ions 7. As shown in FIG. 8, $H^+$, $H_2^+$, $O^+$, $O^{2+}$, $Si^+$, $Si^{2+}$, $Si^{3+}$, $Si^{4+}$, $Si_2^+$, and $SiO^+$ ions were detected on the surface of Si.

ANALYSIS EXAMPLE 2

The surface (100) of silicon (Si) was subjected to wet processing by so-called Shiraki method, and then annealed at 900° C. for 3 minutes. Xe ions having a valence of 50 ($Xe^{50+}$) were irradiated on the surface of the object to be measured 5 under the same conditions as analysis example 1.

Figure 9:
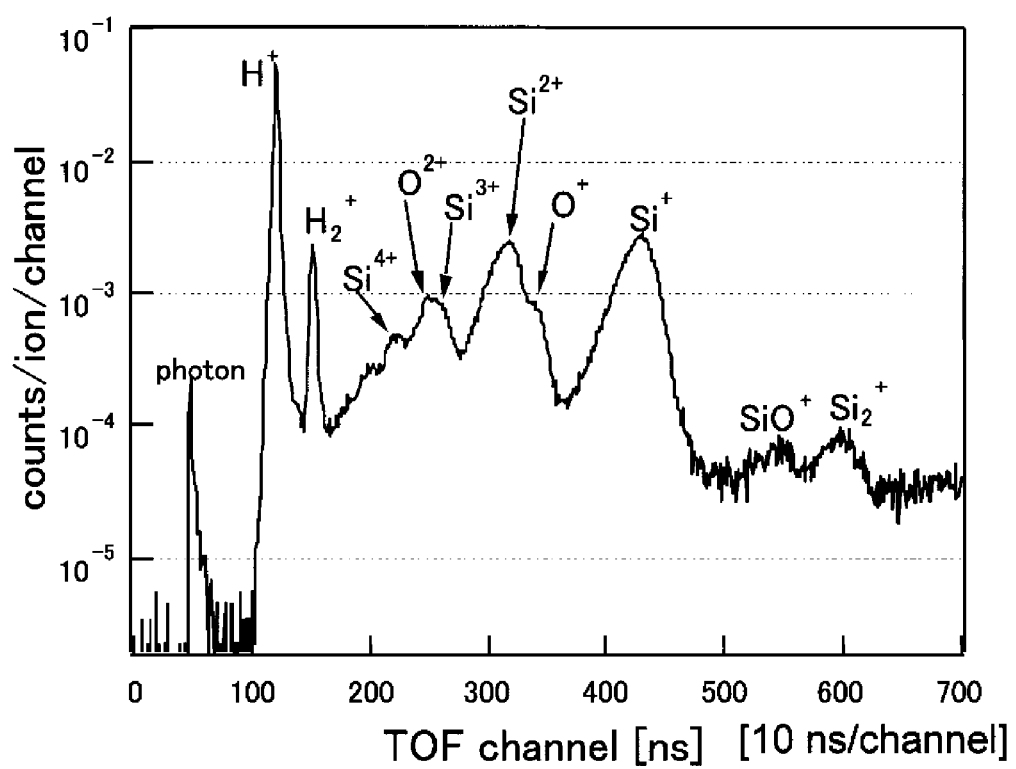
FIG. 9 is a profile of analysis example 2 obtained by TOF-SIMS.

FIG. 9 is a profile of analysis example 2 obtained by TOF-SIMS. The horizontal and vertical axes in FIG. 9 represent the same factors as FIG. 8. As shown in FIG. 9, $H^+$, $H_2^+$, $O^+$, $O^{2+}$, $Si^+$, $Si^{2+}$, $Si^{3+}$, $Si^{4+}$, $Si_2^+$, and $SiO^+$ ions were detected on the surface of Si.

ANALYSIS EXAMPLE 3

After the surface (100) of silicon (Si), which was the object to be measured 5, was heated at 1200° C. for 12 hours for cleaning, Xe ions having a valence of 50 ($Xe^{50+}$) were irradiated on the surface under the same conditions as analysis example 1.

FIG. 10 is a profile of analysis example 3 obtained by TOF-SIMS. The horizontal and vertical axes in FIG. 10 represent the same factors as FIG. 8. As shown in FIG. 10, $H^+$, $H_2^+$, $Si^+$, $Si^{2+}$, $Si^{3+}$, $Si^{4+}$ and $Si_2^{30}$ ions were detected on the surface of Si.

COMPARISON BETWEEN ANALYSIS EXAMPLES 1 to 3

Secondary ions 7 detected on the surface of Si in analysis examples 1 and 2 are found to be of the same type. In addition, the counts of $H^+$ ions detected are almost the same.

Meanwhile, in analysis example 3, $O^+$, $O^{2+}$ and $SiO^+$ ions, which were detected in analysis examples 1 and 2, were not detected on the surface of the objects measured 5. It was also found that the count of $H^+$ ions detected was smaller by an order than those detected in analysis examples 1 and 2. From these results, it was found that the amount of hydrogen on the surface of Si in analysis example 3 was extremely small.

ANALYSIS EXAMPLE 4

After the surface (100) of silicon (Si), which was the object to be measured 5, was heated at 1200° C. for 12 hours for cleaning, Xe ions having a valence of 50 ($Xe^{50+}$) were irradiated on the surface under the same conditions as analysis example 1.

Figure 11:
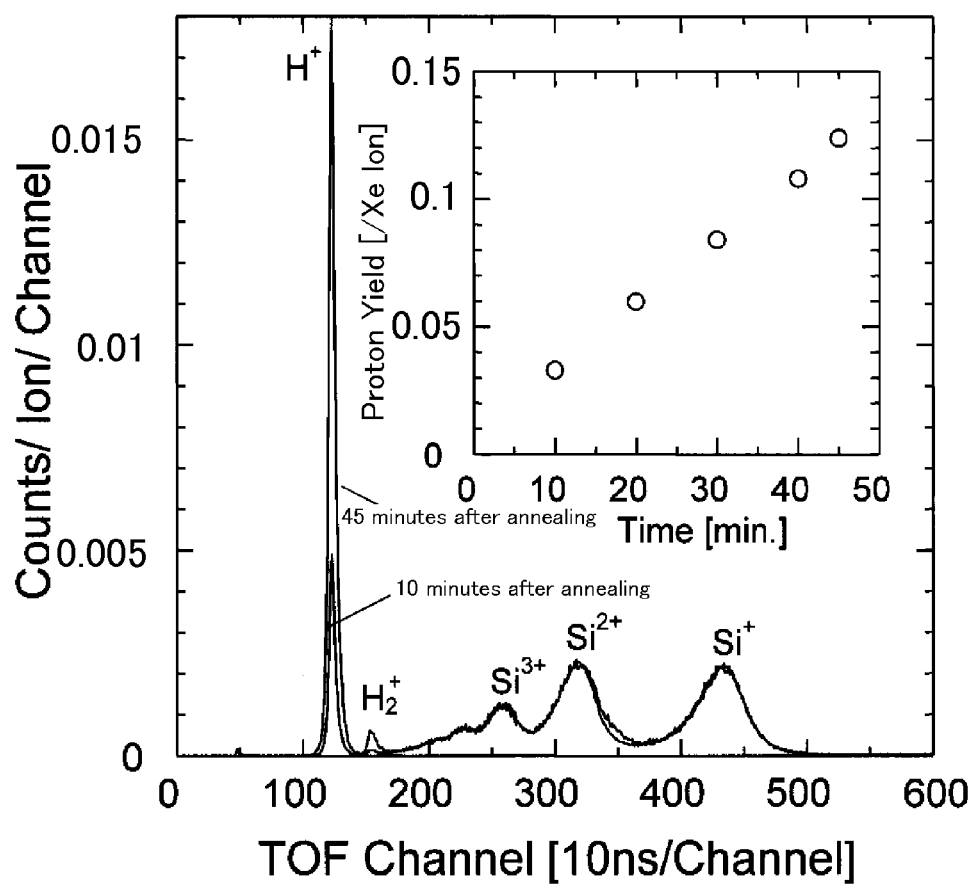
FIG. 11 is a profile of analysis example 4 obtained by TOF-SIMS.

FIG. 11 illustrates the profile of analysis example 4 obtained by TOF-SIMS. FIG. 11 illustrates the profiles at the time when 10 minutes elapsed and when 45 minutes elapsed after the surface of Si (100) was annealed, with the horizontal and vertical axes representing the same factors as those in FIG. 8. As shown in FIG. 11, $H^+$, $H_2^+$, $Si^+$, $Si^{2+}$ and $Si^{3+}$ ions were detected on the surface of Si, and $H^+$ count increased significantly after the elapse of 45 minutes.

The diagram inserted in FIG. 11 illustrates the dependency of $H^+$ ion yield after annealing on time, with the horizontal axis representing the elapsed time after annealing (min.) and the vertical axis representing $H^+$ ion yield. The diagram indicates that almost no $H^+$ ions were detected immediately after the annealing, and that after the elapse of time of 10, 20, 30, 40, and 45 minutes, $H^+$ ions were detected, with their yield increasing with time.

From the result of analysis example 4, it was found that the amount of hydrogen increased with the elapse of time from immediately after cleaning of the surface of Si.

As shown in analysis example 4, the clean surface formed on the surface of Si, namely the object to be measured 5, which can rarely be analyzed with conventional techniques requiring long measurement time, was assessed accurately.

ANALYSIS EXAMPLE 5

After the surface (111) of silicon (Si), which was the object to be measured 5, was heated at 1200° C. for 5 seconds three times, Xe ions having valences of 29, 34, 38, 44, and 50 ($Xe^{50+}$) were irradiated on the surface at the accelerating voltage of 3 kV.

Figure 12:
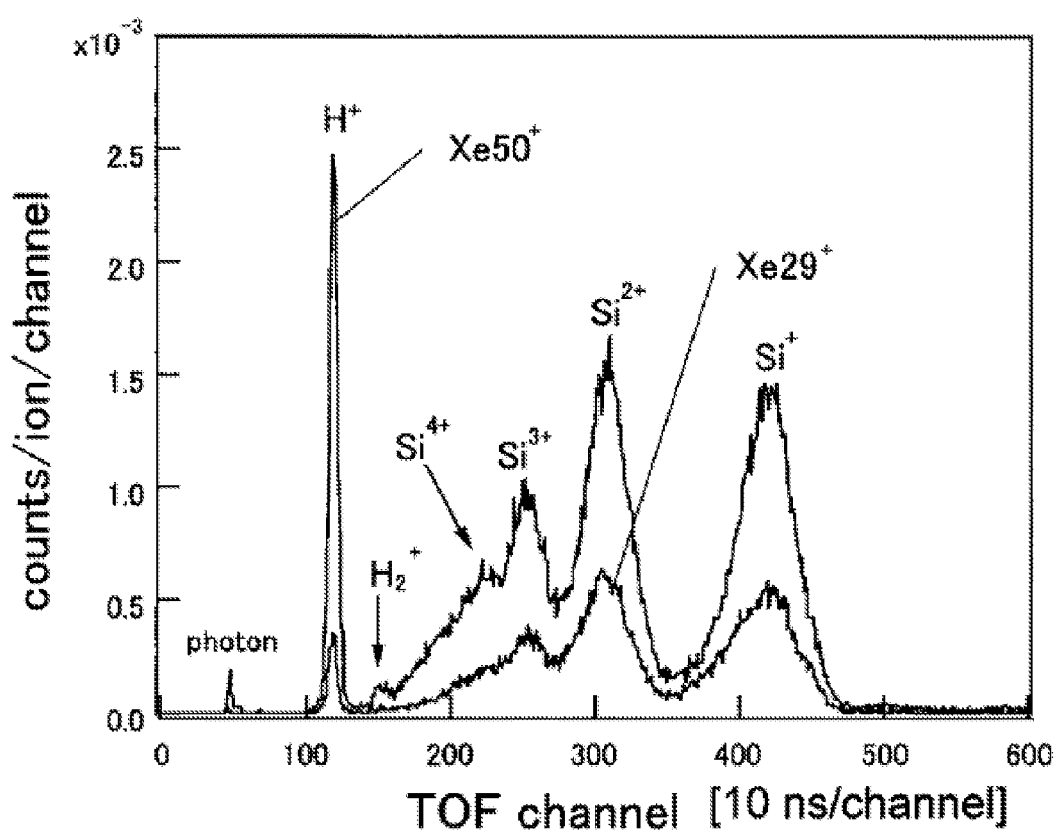
FIG. 12 illustrates the profile obtained by TOF-SIMS when Xe ions having a valence of 29 ($Xe^{29+}$) and those having a valence of 50 ($Xe^{50+}$) were irradiated in analysis example 5.

FIG. 12 illustrates the profile obtained by TOF-SIMS when Xe ions having a valence of 29 ($Xe^{29+}$) and those having a valence of 50 ($Xe^{50+}$) were irradiated. In FIG. 12, the horizontal axis represents the time of flight (ns), and the vertical axis represents the count of secondary ions 7 detected. As shown in FIG. 12, as a result of irradiating Xe ions having a valence of 29 ($Xe^{29+}$), $H^+$, $Si^{3+}$, $Si_2^+$ and $Si^+$ ions were detected on the surface of Si. The ions detected on the surface of Si as a result of irradiating Xe ions having a valence of 50 ($Xe^{50+}$) included $H_2^+$ and $Si^{4+}$ ions, in addition to those detected as a result of irradiating Xe ions having a valence of 29 ($Xe^{29+}$), and the count of ions detected was higher.

Figure 13:
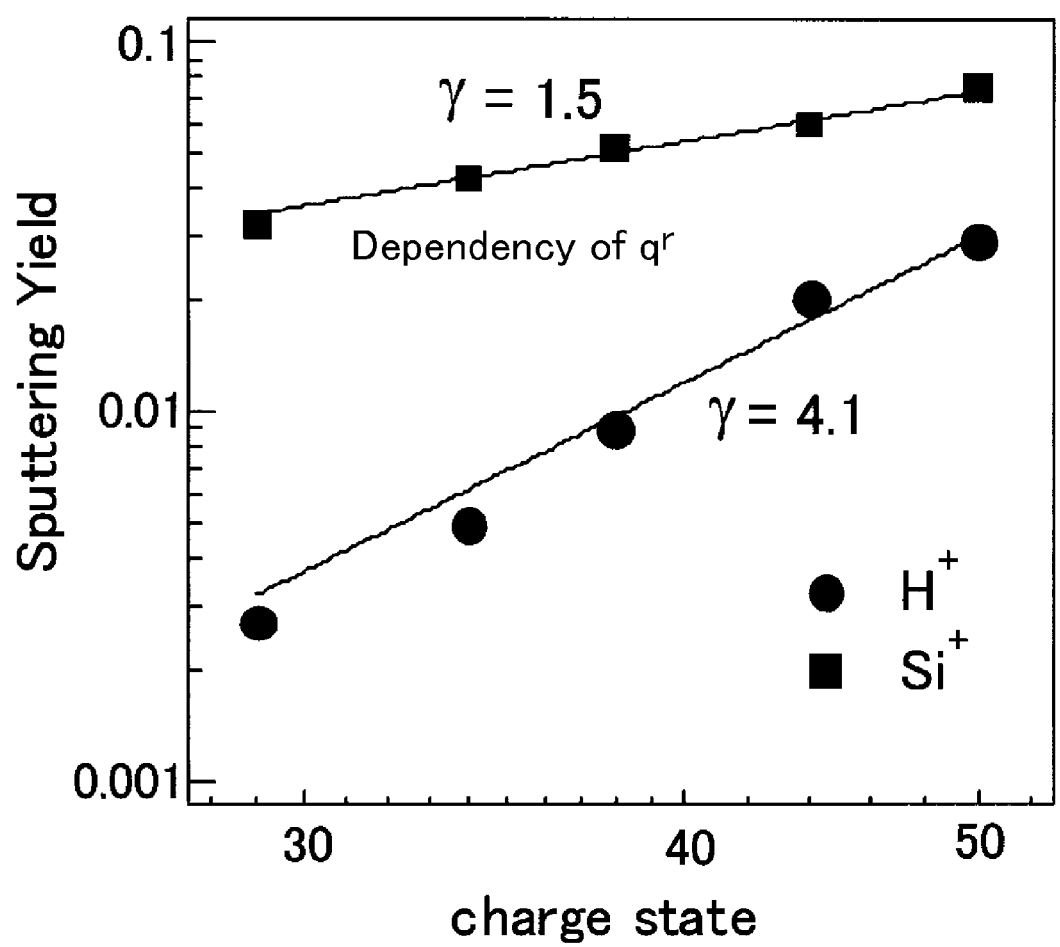
FIG. 13 illustrates the dependency of sputtering yield of $H^+$ and $Si^+$ ions detected in analysis example 5.

FIG. 13 illustrates the dependency of sputtering yield of $H^+$ and $Si^+$ ions detected in analysis example 5 on the valence. In FIG. 13, the horizontal axis represents the valence of Xe ions irradiated, whereas the vertical axis represents the sputtering yield of $H^+$ and $Si^+$ ions. As shown in FIG. 13, the sputtering yield of $H^+$ ions increased in proportion to the valence q raised to the 4.1st power, namely $q^{4.1}$. Similarly, the sputtering yield of $Si^+$ ions increased in proportion to the valence q raised to the 1.5th power, namely $q^{1.5}$.

ANALYSIS EXAMPLE 6

I ions ($I^{15+}$, $I^{20+}$, $I^{25+}$, $I^{30+}$, $I^{35+}$, $I^{40+}$, $I^{45+}$, $I^{50+}$) of various valences increasing in steps of 5 within the range 15 to 50 were irradiated onto the surface of $SiO_2$, which was the object to be measured 5 at the accelerating voltage of 3 kV.

Figure 14:
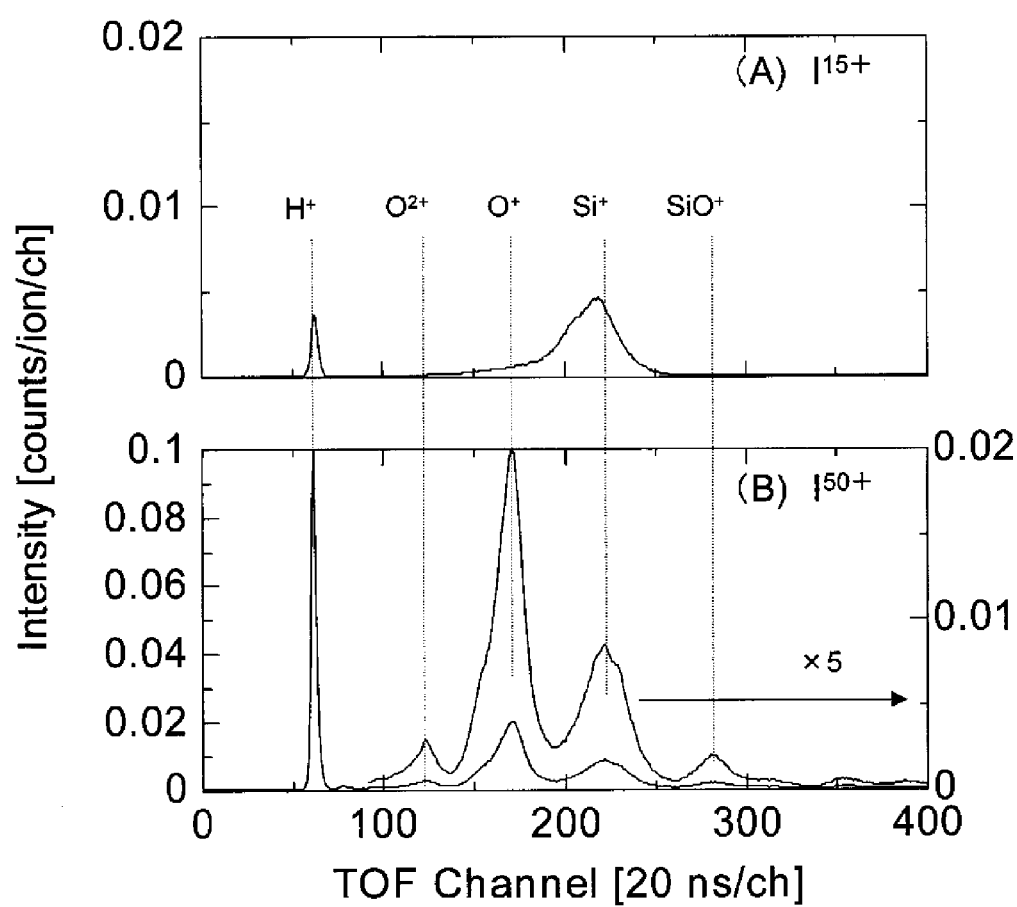
FIG. 14 illustrates the profile obtained by TOF-SIMS when I ions having a valence of 15 ($I^{15+}$) and those having a valence of 50 ($I^{50+}$) were irradiated in analysis example 6.

FIG. 14 illustrates the profile, in the example 6, obtained by TOF-SIMS when I ions having a valence of 15 ($I^{15+}$) and those having a valence of 50 ($I^{50+}$) were irradiated. In FIG. 14, the horizontal axis represents the time of flight (ns), whereas the vertical axis represents the count of secondary ions 7 detected. As shown in FIG. 14, $H^+$ and $Si^+$ ions were detected on the surface of Si when I ions having a valence of 15 ($I^{15+}$) were irradiated. The ions detected on the surface of Si as a result of irradiating I ions having a valence of 50 ($I^{50+}$) included $O^+$, $O^{2+}$ and $SiO^+$, in addition to those ($H^+$, $Si^+$) detected as a result of irradiating I ions having a valence of 15 ($I^{15+}$), and the count of ions detected was higher.

The surface analysis of $SiO_2$ film using multicharged ions in analysis example 6 is characterized in that oxygen is detected as positive ions. Meanwhile, in conventional SIMS analysis using monovalent ion as irradiation source, oxygen was detected as negative ions.

Figure 15:
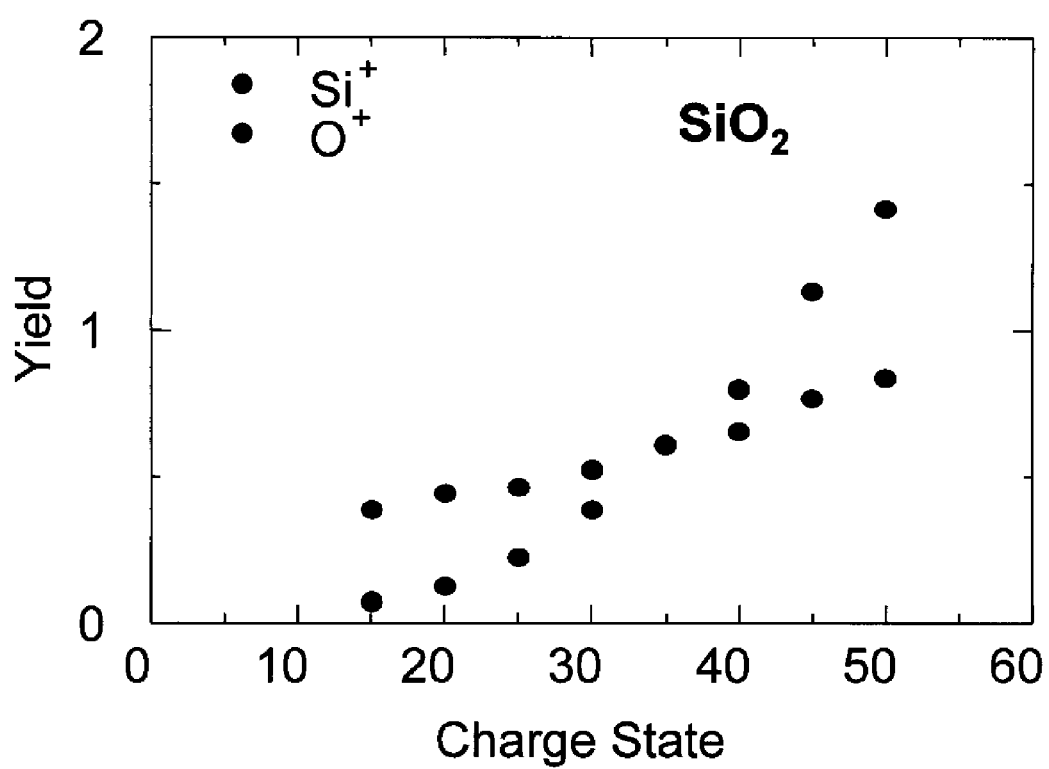
FIG. 15 illustrates the dependency of the sputtering yield of $Si^+$ and $O^+$ ions detected in analysis example 6.

FIG. 15 illustrates the dependency of the sputtering yield of $Si^+$ and $O^+$ ions detected in analysis example 6 on the valence. In FIG. 15, the horizontal axis represents the valence of I ions irradiated, whereas the vertical axis represents the sputtering yield of $Si^+$ and $O^+$ ions. As shown in FIG. 15, the sputtering yield of $Si^+$ ions increased approximately in proportion to the valence q.

Meanwhile, the sputtering yield of $O^+$ ions increased in proportion to the valence q raised to the 2.5th power, namely $q^{2.5}$. When the valence was larger than 35 (q>35), the yield of $O^+$ ions was found to be higher than that of $Si^+$ ions. Consequently, if the valence was 50 ($I^{50+}$), the sputtering yield of $O^+$ was approximately twice that of $Si^+$, which was the yield of secondary ions 7 reflecting the stoichiometric composition of $SiO_2$.

ANALYSIS EXAMPLE 7

I ions ($I^{15+}$, $I^{20+}$, $I^{25+}$, $I^{30+}$, $I^{35+}$, $I^{40+}$, $I^{45+}$, $I^{50+}$) of various valences increasing in steps of 5 within the range 15 to 50 were irradiated as in the case of analysis example 6, except that the object to be measured 5 was $TiO_2$ and not $SiO_2$, at the accelerating voltage of 175 keV. In the case the object to be measured 5 was $TiO_2$, $Ti^+$ and $O^+$ ion signals were obtained when the valence was 25 or higher.

Figure 16:
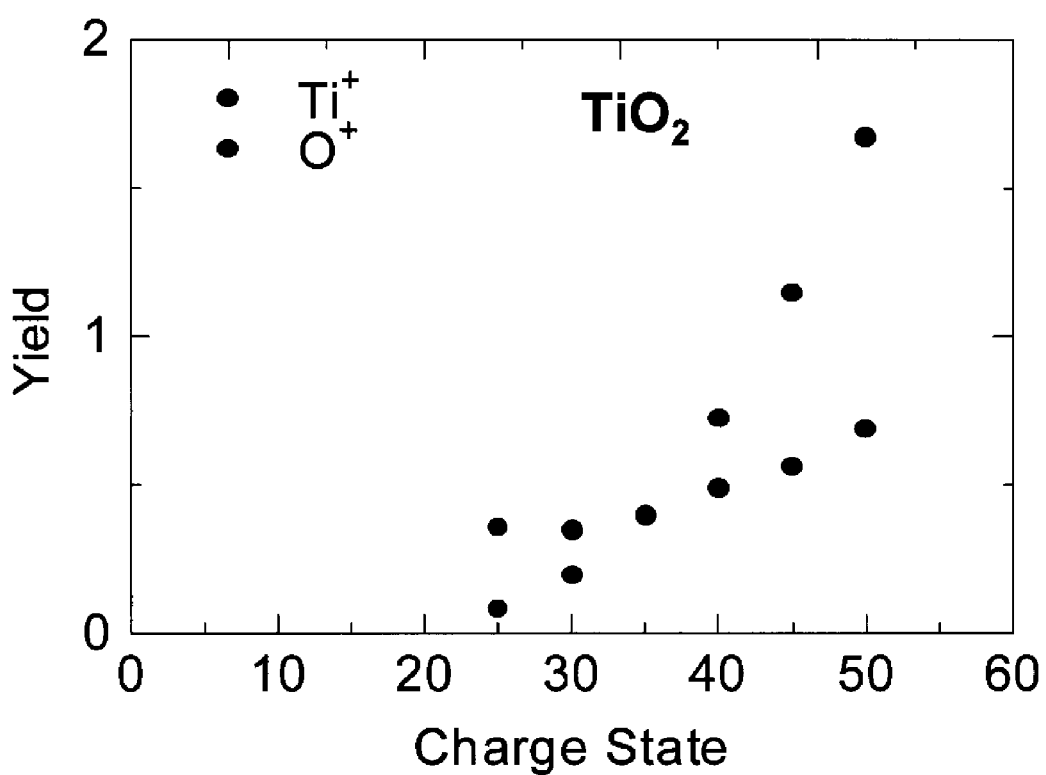
FIG. 16 illustrates the dependency of the sputtering yield of $Ti^+$ and $O^+$ ions detected in analysis example 7.

FIG. 16 illustrates the dependency of the sputtering yield of $Ti^+$ and $O^+$ ions detected in analysis example 7 on the valence. In FIG. 16, the horizontal axis represents the valence of I ions irradiated, whereas the vertical axis represents the sputtering yield of $Ti^+$ and $O^+$ ions. As shown in FIG. 16, the sputtering yield of $Ti^+$ ions increased almost proportionally when the valence q was 30 or higher.

Meanwhile, the sputtering yield of $O^+$ ions increased in proportion to the valence q raised to the 4th power, namely $q^4$. If the valence exceeds 35 (q>35), the yield of $O^+$ ions was found to be higher than that of $Ti^+$ ions. Consequently, if the valence is 50 ($I^{50+}$), the sputtering yield of $O^+$ was approximately twice that of $Ti^+$, which was the yield of secondary ions 7 reflecting the stoichiometric composition of $TiO_2$.

The present invention are not limited to those described above, and various variations are allowed within the range described in the scope of claims. It goes without saying that those variations are included in the scope of the present invention. For example, the shape of the multicharged ion guide 26, the structure of the vacuum chamber 2, and the configuration of an observing equipment to be added can be modified as required depending on the object to be measured 5.

REFERENCE SIGNS LIST

1: Surface analyzer
2: Vacuum chamber
3: Source for generating multicharged ions
4: Beam of multicharged ions
5: Object to be measured
6: Stage for object
7: Secondary ion
8: Mass analyzer
9: Secondary electron
10: Secondary electron detector
10A, 10B: Secondary electron detecting apparatus
10C: Grid
12: Controller of mass analyzer
14: Lens
15: Fright tube
16: Secondary ion detecting apparatus
16A: Measurement stop signal
20: Multichannel analyzer
21: Analysis start signal generating means
22: Computer
24: AND circuit
24A, 24B: Input
24C: Output
26: Multicharged ion guide
26C: End portion
31: First vacuum chamber
31$a$: Ultrahigh vacuum flange
31$b$: Support arm
32: Second vacuum chamber
33: Vacuum pumping unit for the first vacuum chamber
34: Vacuum pumping unit for the second vacuum chamber
35: Superconducting magnet
35$a$: First coil portion
35$b$: Second coil portion
36: Drift tube
37, 44: magnetic shield
40: Ion source electrode
41: Electron source
41$a$: Filament (cathode) electrode
41$b$: Focus electrode
41$c$: Anode electrode
41$d$: Snout electrode
41$e$: Electrical porcelain
42: Collector
43: Bucking coil
46: Gas ion infeed means
46$a$: Gas source
46$b$: Flow controller
46$c$: Piping
48: Solid ion infeed means

What is claimed is:

1. A method of analyzing a surface of a compound having an unknown composition ratio, comprising:
   a first step of finding a relation between a valence of a multicharged ions beam and respective counts of secondary ions generated from specific elements on a surface of a standard compound in response to irradiation of the multicharged ion beam thereonto, by radiating the multicharged ions beam to the standard compound at multiple times while changing the valence of the multicharged ions beam each time, the standard compound being constituted of same constituent elements as the compound to be measured and having a known stoichiometric composition ratio;
   a second step of finding a valence of the multicharged ions beam at which a count ratio of secondary ions from the specific elements is substantially equal to the stoichiometric composition ratio of the standard compound based on the relation between the valence of the multicharged ions beam and the respective counts of the secondary ions found in the first step; and
   a third step of performing surface analysis of the compound with the unknown composition ratio by radiating a multicharged ions beam having the valence found in the second step to the compound with the unknown composition ratio.

2. The method according to claim 1, wherein the valence of the multicharged ions beam is changed within a range 15 or higher in the first step.

3. The method according to claim 1, wherein, in the first step, a pulse of single multicharged ion having a valence of 15 or higher is irradiated onto the standard compound to repetitively perform a measurement per pulse, pieces of data obtained by this measurement are integrated, and when the average value converges on a certain value, irradiation of the pulse of single multicharged ion is stopped.

4. The method according to claim 1, wherein the valence of the multicharged ions beam is changed up to 50 in the first step.

* * * * *